United States Patent [19]

Morpeth et al.

[11] Patent Number: 5,125,967
[45] Date of Patent: Jun. 30, 1992

[54] BIOCIDAL COMPOSITION COMPRISING AN ISOTHIAZOLINONE DERIVATIVE AND A SUBSTITUTED UREA OR HALOGENATED AROMATIC ALKYL SULPHOXIDE OR SULPHONE

[75] Inventors: Fraser F. Morpeth, Bury; Malcolm Greenhalgh, Ripponden, all of England

[73] Assignee: Imperial Chemical Industries PLC, London, England

[21] Appl. No.: 502,081

[22] Filed: Mar. 29, 1990

[30] Foreign Application Priority Data

Mar. 31, 1989 [GB] United Kingdom ............... 8907298

[51] Int. Cl.$^5$ .............................................. C09C 5/14
[52] U.S. Cl. ............................ 106/18.22; 106/18.21; 106/18.23; 106/18.24; 106/18.33; 106/18.34; 424/405; 514/445; 514/594; 514/596; 514/706; 514/708; 514/709; 548/213
[58] Field of Search ............... 106/18.21, 18.22, 18.23, 106/18.24, 18.33, 18.34; 424/405; 548/213; 514/445, 594, 596, 706, 708, 709

[56] References Cited

U.S. PATENT DOCUMENTS

| | | | |
|---|---|---|---|
| 2,655,445 | 10/1953 | Todd | 71/120 |
| 2,768,971 | 10/1956 | Jones | 564/53 |
| 3,290,353 | 12/1966 | Battershell et al. | 558/419 |
| 3,296,272 | 1/1967 | Johnston | 546/295 |
| 3,331,735 | 7/1967 | Battershell et al. | 514/525 |
| 3,371,011 | 2/1968 | Johnston | 514/347 |
| 3,517,022 | 6/1970 | Miller et al. | 548/209 |
| 3,632,859 | 1/1972 | Crovetti | 568/33 |
| 3,663,623 | 5/1972 | Crovetti et al. | 568/35 |
| 3,761,488 | 9/1973 | Lewis et al. | 548/213 |
| 3,821,389 | 6/1974 | Grivas | 106/18.32 |
| 3,849,430 | 11/1974 | Lewis et al. | 106/18.32 |
| 3,929,561 | 12/1975 | Shema et al. | 106/18.33 |
| 3,950,349 | 4/1976 | Buckley et al. | 548/209 |
| 4,031,055 | 6/1977 | Dupont et al. | 106/18.32 |
| 4,105,431 | 8/1978 | Lewis et al. | 106/18.32 |
| 4,129,448 | 12/1978 | Greenfield et al. | 106/18.32 |
| 4,165,318 | 8/1979 | Greenfield et al. | 548/213 |
| 4,209,522 | 6/1980 | Mixan et al. | 106/18.33 |
| 4,466,975 | 8/1984 | Magami et al. | 106/18.32 |

FOREIGN PATENT DOCUMENTS

| | | | |
|---|---|---|---|
| 51-002093 | 1/1976 | Japan | 106/18.33 |
| 56-071009 | 6/1981 | Japan | 106/18.33 |
| 58-150577 | 9/1983 | Japan | 106/18.32 |
| 691403 | 5/1953 | United Kingdom . |  |
| 692589 | 6/1953 | United Kingdom . |  |
| 1103606 | 2/1968 | United Kingdom . |  |
| 1113634 | 5/1968 | United Kingdom . |  |
| 1191253 | 5/1970 | United Kingdom . |  |
| 1330531 | 9/1973 | United Kingdom . |  |
| 2004747 | 4/1979 | United Kingdom . |  |
| 2087388 | 5/1982 | United Kingdom . |  |

*Primary Examiner*—William R. Dixon, Jr.
*Assistant Examiner*—Anthony J. Green
*Attorney, Agent, or Firm*—William E. Dickheiser

[57] ABSTRACT

A composition comprises an isothiazolinone or an isothiazolothione and a substituted urea or a halogen-containing aromatic alkyl sulphoxide or sulphone. The isothiazolinone derivative can be 1,2-benzisothiazolin-3-one. The substituted urea may be 3-(3,4-dichlorophenyl)-1-1-dimethylurea. The sulphoxide or sulphone may be a sulphone derivative such as di-iodomethyl-4-methylphenyl sulphone. A useful composition comprises 1,2-benzisothiazolin-3-one and the specified urea or sulphone derivative. The composition may include other materials including other compounds having antimicrobial properties.

16 Claims, No Drawings

BIOCIDAL COMPOSITION COMPRISING AN ISOTHIAZOLINONE DERIVATIVE AND A SUBSTITUTED UREA OR HALOGENATED AROMATIC ALKYL SULPHOXIDE OR SULPHONE

The present invention relates to compositions which are useful as industrial biocides.

Industrial biocides are useful to prevent industrial spoilage, in particular that caused by bacteria and fungi. Industrial biocides find application in the preservation of paints, latices, adhesives, leather, wood, metal working fluids and cooling water.

One class of compound which can be used as an industrial biocide is based on the isothiazolinone structure. There are many disclosures of isothiazolinone derivatives which are stated to have useful biocidal properties. U.S. Pat. No. 3,761,488 discloses isothizolinone derivatives in which alkyl, alkenyl, alkynyl, cycloalkyl, aralkyl or aryl groups, which may optionally be substituted, are attached to the nitrogen atom and the 4 and 5 positions are unsubstituted or are substituted with halogen or lower alkyl groups. U.S. Pat. No. 3,517,022 discloses benzisothiazolones in which a carbamoyl group is attached to the nitrogen atom and the benzene ring may be optionally substituted. U.S. Pat. No. 3,950,349 discloses N-thio-substituted isothiazolin-3-one compounds which may be isothiazolin-3-one or benzisothiazolin-3-one derivatives. U.S. Pat. No. 4,165,318 discloses a solution of an isothiazolin-3-one in a polar organic solvent, wherein the solution also contains a stabilising amount of formaldehyde. British Patent Specification 2087388 discloses 4,5-polymethylene-4-isothiazolin-3-one in which the polymethylene chain has three or four carbon atoms.

Another class of compound which is stated to be fungicidal is based on the isothiazolothione structure. British Patent Specification 1113634 discloses compounds of this type or an isomeric form thereof, in which the 4 and 5 positions are unsubstituted or may be substituted with alkyl or aryl groups or which may form a part of a further ring system.

Isothiazolin-3-ones which are unsubstituted on the nitrogen atom are capable of forming salts for example with alkali metal such as sodium and potassium, and with ammonia or amines such as triethanolamine. These salts are generally water-soluble. British Patent Specification 1191253 describes and claims high strength aqueous solutions of crude 1,2-benzisothiazolin-3-one in the form of a mixture of two or more different amine salts thereof, the amines being selected from diethanolamine, triethanolamine, diisopropanol amine, triisopropanolamine and morpholine. British Patent Specification 1330531 discloses compositions of 1,2-benzisothiazolin-3-one in aliphatic, cycloaliphatic or heterocyclic amines which contain 2 to 6 carbon atoms and which are free from hydroxyl and ether groups. British Patent Specification 2004747 discloses solutions of an alkali metal salt of 1,2-benzisothiazolin-3-one in a hydroxylic organic solvent such as propylene glycol, dipropylene glycol and polyethylene glycols.

However such salt solutions require the addition of considerable quantities of extra organic solvent, for example glycols, to be stable enough to be commercially acceptable.

Compounds and compositions of the foregoing types, and related compounds of the same general type, are effective to a varying degree, depending on the particular compound or composition, against a range of bacteria and/or fungi. However, to reduce the cost of using these compounds it is desirable to improve their effectiveness as antimicrobial materials.

Compositions have been proposed which contain more than one compound which has antimicrobial properties. In general such compositions show an aggregate of the properties of the compounds present in the composition. Typically such compositions contain one compound which exhibits useful antibacterial properties together with a different compound which exhibits useful antifungal properties.

We have no found that certain compositions possess surprisingly useful antimicrobial properties.

Thus, according to the present invention there is provided a composition which comprises
(a) at least one isothiazolinone derivative or at least one isothiazolothione derivative, and
at least one compound which is
(b) at least one substituted urea, or
(c) at least one halogen-containing aromatic alkyl sulphoxide or sulphone.

The isothiazolinone or isothiazolothione derivative which is component (a) of the composition is typically a compound of the general formula:

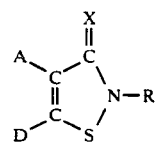

wherein:
X is an oxygen or sulphur atom;
R is a hydrogen atom, a substituted or unsubstituted hydrocarbyl group, a substituted or unsubstituted hydrocarbylthio group, a substituted or unsubstituted hydrocarbyloxy group, a carbamoyl group or a cation;
A is a hydrogen atom, a halogen atom, a cyano group, or a substituted or unsubstituted hydrocarbyl group;
D is a hydrogen atom, a halogen atom, a cyano group, or a substituted or unsubstituted hydrocarbyl group; or
A and D, together with the carbon atoms to which they are attached, form a five- or six-membered ring, which may optionally be substituted.

Preferably component (a) is at least one isothiazolinone derivative, that is a compound in which X is an oxygen atom. If the groups R, A and D are, or contain, substituted hydrocarbyl groups, the substituents are typically halogen, alkoxy or alkylthio, particularly those in which the alkyl groups contain 1 to 4 carbon atoms. If R is a carbamoyl group, this is of the general type —CONHR$^1$ where R$^1$ is a hydrogen atom or a hydrocarbyl group, which may be substituted. It is generally preferred that the group R is a hydrogen atom or a lower alkyl group, that is an alkyl group containing 1 to 4 carbon atoms. R is especially hydrogen or a methyl group.

A and D may, together with the carbon atoms to which they are attached, form a five- or six-membered ring, which may be substituted, the substituents typically being halogen, alkyl, alkoxy or alkylthio groups. The ring thus obtained may contain a heteroatom, for example a nitrogen atom but in general A and D form a hydrocabon ring such as a benzene, cyclopentene or cyclohexene ring. Alternatively, A and D are separate groups and one or both of A and D can be a hydrogen atom. It is generally preferred that at least one of A and D is other than a hydrogen atom and is, particularly, a halogen atom, for example chlorine or a lower alkyl group.

Compounds which can be used as component (a) of the mixture include 2-methylisothiazolin-3-one (R is methyl, A and D are both hydrogen); 5-chloro-2-methylisothiazolin-3-one (R is methyl, A is hydrogen and D is chlorine); mixtures of the foregoing two compounds; 4,5-dichloro-2-methylisothiazolin-3-one (R is methyl and A and D are both chlorine); 1,2-benzisothiazolin-3-one (R is hydrogne and A and D, together with the carbon atoms to which they are attached, form a benzene ring); 4,5-trimethylene-4-isothiazolin-3-one (R is hydrogen and A and D, together with the carbon atoms to which they are attached, form a cyclopentene ring); and 2-methyl-4,5-trimethylene-4-isothiazolin-3-one (R is methyl and A and D, together with the carbon atoms to which they are attached, form a cyclopentene ring).

In component (a), if R is a cation this may be a cation having a valency of more than one but is particularly a monovalent cation such as an alkali metal, an amine or quaternary ammonium cation. As noted previously herein, such materials are generally water-soluble and hence can be used in an aqueous medium.

Component (b) of the composition of the present invention is at least one substituted urea and is typically a urea which contains at least one substituent group on each nitrogen atom. One class of urea compound which may be used contains one substituent group which is, or which contains, an aromatic group (an "aromatic substituent") and wherein no other substituent is attached to the nitrogen to which the aromatic substituent is attached. One or two substituents may be attached to the other nitrogen and these substituents are typically alkyl, alkenyl, alkynyl, alkoxy, or cycloalkyl groups. Substituted ureas which may be used as component (b) are typically of the general formula:

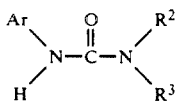

wherein
Ar is an aryl, substituted aryl, heterocyclic or substituted heterocyclic group;
$R^2$ is an alkyl, substituted alkyl, alkenyl, substituted alkenyl, alkynyl, substituted alkynyl, cycloalkyl, substituted cycloalkyl, alkoxy or substituted alkoxy group; and
$R^3$ is a hydrogen atom or a group as defined for $R^2$.

The substituted groups may contain one or more substituents selected from a hydrocarbon group, a halogen atom, a hydrocarbonoxy group, a hydroxy group, and an alkylaminosulphonyl group, or a mixture of such substituents.

The group Ar may be an unsubstituted aryl group such as a phenyl group but generally contains at least one substituent which is a halogen atom, an alkyl group, an alkoxy group or an aryloxy group which may itself be substituted. Thus, the group Ar may be, for example, a phenyl, 4-chlorophenyl, 3,4-dichlorophenyl, 4-isopropylphenyl, 3-chloro-4-bromophenyl, 3-chloro-4-methylphenyl, 4(4'-chlorophenoxy)phenyl or 4(4'-methoxyphenoxy)phenyl group. If the group Ar is, or includes, a heterocyclic group, it may be, for example, benzothiazol-2-yl group or it may be a heterocyclic group having aromatic characteristics such as a pyridyl group.

The groups $R^2$ and $R^3$ are typically unsubstituted. Generally $R^2$ and $R^3$ each contain not more than six carbon atoms, especially not more than four carbon atoms. If $R^3$ is other than a hydrogen atom, the groups $R^2$ and $R^3$ can be the same or different. Typically $R^3$ is a hydrogen atom or a methyl group. The group $R^2$ may be, for example, a methyl, n-butyl, methoxy, 2-methylcyclohexyl, or 3-butynyl group.

Substituted ureas which can be used as component (b) include
3-(3,4-dichlorophenyl)-1,1-dimethylurea,
3-(3,4-dichlorophenyl)-1-methyl-1-n-butylurea,
3-(3-chloro-4-bromophenyl)-1-methyl-1-methoxyurea,
3-[4-(4'-chlorophenoxy)phenyl]-1,1-dimethylurea,
3-[4-(4'-methoxyphenoxy)phenyl]-1,1-dimethylurea,
3-(4-chlorophenyl)-1-methyl-1-(3-butynyl)urea,
3-phenyl-1-(2-methylcyclohexyl)urea, and
3-(benzothiazol-2-yl)-1-methylurea.

Other substituted ureas include
3-(4-isopropylphenyl)1,1-dimethylurea,
3-(3,4-dichlorophenyl)1-methyl-1-methoxyurea,
3-(3-chloro-4-methylphenyl)-1,1-dimethylurea,
1,1-dimethyl-3-phenylurea,
3-(4-chlorophenyl)-1,1-dimethylurea,
3-(3-chloro-4-methoxyphenyl)-1,1-dimethylurea,
1,1-dimethyl-3-(4-trifluoromethylphenyl)urea,
3-(3-tertiary butylcarbamoyloxy)-phenyl-1,1-dimethylurea,
1,1-dimethyl-3-(4-trifluoromethylphenyl)urea,
3-[3-chloro-4-(chlorodifluromethylthio)phenyl]-1,1-dimethylurea,
3-(3-[1',1',2',2'-tetrafluoroethoxy]phenyl)-1,1-dimethylurea, and
3-(3-chloro-4-trifluoromethoxyphenyl)-1,1-dimethylurea.

Compositions having useful properties have been obtained in which component (b) is 3-(3,4-dichlorophenyl)-1,1-dimethylurea.

Substituted ureas which can be used as component (b) can be prepared by known procedures, for example as described in British Patents 691403 and 692589 and U.S. Pat. Nos. 2,655,455 and 2,768,971.

Suitable materials for use as component (c) have the general formula:

wherein
$Ar^1$ is an aryl, substituted aryl, heterocyclic or substituted heterocyclic group;
$R^4$ is an alkyl, substituted alkyl, aryl or substituted aryl group;
x has a value of one or two; and
at least one of the groups $Ar^1$ and $R^4$ contains at least one halogen substituent.

The substituents which may be present in the groups $Ar^1$ and $R^4$ include at least one halogen atom, hydrocarbyl group or hydrocarbyloxy group. $Ar^1$ or $R^4$, or both, contain at least one halogen atom substituent.

In one class of compound which can be used as component (c), $Ar^1$ is a heterocyclic group particularly a substituted heterocyclic group having aromatic characteristics such as a pyridine ring which contains at least one halogen substituent, particularly at least two halogen atoms, for example three halogen atoms. In such a compound it is preferred that $R^4$ is an unsubstituted alkyl group containing 1 to 12 carbon atoms. Compounds of this type, and the preparation of such compounds, are described in more detail in British Patent 1103606, and U.S. Pat. Nos. 3,296,272 and 3,371,011. As is described in more detail in the aforementioned patents, compounds of this type can be prepared by the oxidation of the corresponding thiopyridine compound. Suitable compounds of this type include those in which $Ar^1$ is a pyridine ring which contains three or four halogen substitutents, $R^4$ is a lower alkyl group, that is an alkyl group containing up to six carbon atoms and the value of x is two. Compounds of this type include 2,3,5,6-tetrachloro-4-(methylsulphonyl)pyridine; 2,3,6-trichloro-4-(methylsulphonyl)pyridine and 2,3,5,6-tetrachloro-4-(isopropylsulphonyl)pyridine.

In a further class of compound which can be used as component (c), $Ar^1$ contains an aryl group, $R^4$ is a halogen substituted methyl group and x has a value of two. Compounds of this general type, and the preparation thereof, are described in more detail in U.S. Pat. Nos. 3,632,859 and 3,663,623. As described in U.S. Pat. No. 3,632,859, compounds of this type can be prepared by halogenating a sulphonyl acetic acid, for example using sodium hypoiodite in sodium hydroxide solution. The procedure of U.S. Pat. No. 3,663,623 differs in that the halogenating step is carried out using iodine monochloride in an essentially neutral solution. Suitable compounds of this type include those in which $Ar^1$ is an alkyl substituted aryl group such as a 4-methylphenyl group and $R^4$ is a diiodomethyl group.

Compositions having useful properties have been obtained in which component (c) is di-iodomethyl-4-methylphenyl sulphone.

As a particular embodiment of the present invention there is provided a composition comprising (a) 1,2-benzisothiazolin-3-one with either 3-(3,4-dichlorophenyl)-1,1-dimethylurea or di-iodomethyl-4-methylphenyl sulphone.

For convenience hereafter, the term "the further component" will be used in respect of component (b) or component (c) or mixture of components (b) and (c).

The relative proportions of the components of the composition can vary and compositions having useful properties can be obtained which contain from 1% by weight of component (a) or the further component and, correspondingly, up to 99% by weight of the further component or component (a). The preferred proportions are dependent on the compounds used as component (a) and the further component, and also the particular system in which the mixture is to be used. In general the composition contains at least 2% by weight of each component and especially at least 8% by weight of each component.

The compositions of the present invention have antimicrobial properties. We have found that compositions in accordance with the present invention are active against both bacteria and fungi. Furthermore, compositions in accordance with the present invention are such that the sum of the fractional inhibitory concentration (FIC) for all the components of the composition is less than one and, with preferred compositions is less than 0.7. Especially preferred compositions are those in which the sum of the FIC for all the components of the composition is not more than 0.6. The FIC is the ratio of the concentration of an individual component to the minimum inhibitory concentration of that component. It will be appreciated that if the value of the sum of the FIC for all the components of the composition is less than one, the composition is synergistic, the extent of synergy being indicated by the amount by which the sum of the FIC is below one. We have found that some compositions in accordance with the present invention are such that the sum of the FIC can be less than 0.6.

The compositions of the present invention have antimicrobial properties and are suitable for use as industrial biocides.

The compositions of the present invention provide good wet state preservation and hence may be used as a cutting fluid preservative and also in cooling water applications. Wood and leather preservation is another field of application of the compositions. The compositions of the present invention can also be incorporated into paint, as paint film fungicide that can be used without addition of a bactericide.

The materials which are component (a) and the further component of the composition of the present invention are soluble in many polar solvents, although the solubility is dependent on the nature of the particular compounds which are present in the composition. However, many of the compounds are soluble in water, alcohols, ethers, ketones and other polar solvents or mixtures thereof.

The compositions of the present invention may be used alone as an antimicrobial material but may also be used in, or on, a suitable carrier material.

Thus, as a further aspect of the present invention there is provided a biocide composition comprising a carrier and an effective amount of a composition of component (a) together with component (b) or component (c) or both components (b) and (c) in accordance with the invention.

The carrier is typically a material which shows little, if any, antimicrobial activity and may be, or include, a material which is susceptible to the growth of microorganisms, particularly fungi. The carrier may be a liquid medium and the biocide composition may be a solution, suspension or emulsion of the composition of component (a) and the further component in a liquid carrier. The carrier may be water, in which one or both of component (a) and the further component are essentially insoluble, or may be a liquid such as acetic acid, N,N-dimethylformamide, propylene glycol, dimethyl sulphoxide or N-methyl-2-pyrrolidone in which at least one, and preferably both, of component (a) and the further component are soluble. Alternatively, a mixture of liquids may be used, one being a solvent for component (a) and the further component and the other being a non-solvent for both components, and using such a mixture the composition typically comprises an emulsion or droplets of a solution of component (a) and the further component in the solvent therefor dispersed in the non-solvent. If a suspension or emulsion is used, this conveniently contains a surface active agent which is effective to maintain the non-continuous phase as a suspension or emulsion. Any surface active agent which is effective as a dispersant or emulsifier and is known for use in biocide compositions may be used such as, for example alkylene oxide copolymers, and alkylene oxide adducts of fatty alcohols, alkyl phenols and amines such as ethylene diamine. Other surface active agents which can be used include sodium lignosulphonate, EO/-

PO/EO block copolymers, ethylene oxide condensates with nonyl phenol or beta-naphthol, PO/EO copolymer condensates with nonyl phenol or ethylene diamine and condensates of napthalene beta-sulphonic acid and formaldehyde. The surfactant is typically present in an amount of from 0.1 to 20% by weight of the weight of the total dispersion or emulsion in which the surfactant is to be incorporated. The dispersion or emulsion may include, in addition to the surfactant, other components which are known for inclusion in biocide compositions such as thickening agents. Materials which can be used as thickening agents include polysaccharide xanthan gum, sodium magnesium silicate, heteropolysaccharide, alginates, carboxymethyl cellulose, gum arabic, polyacrylic acid and polyvinyl alcohol.

Alternatively, or additionally, the composition may include one or more solid components, which may act as carriers or diluents. Solid materials which may be used as the optional component include inorganic materials such as metal oxides or mixtures or compounds thereof, for example aluminium oxide, silicon oxide, titanium dioxide, zinc oxide, talc, pyrophyllite, gypsum, kieselguhr, chalk, diatomaceous earth, bentonite and fuller's earth and organic materials such as wheat flour, soybean flour, wood flour, walnut shell flour and lignin. The solid material is preferably in a finely divided form and typically has an average particle size of not more than 5 micrometres. Any optional solid may be added to the composition in an amount of from 1% up to 95% by weight of the total weight of the composition plus optional solid and in general the optional solid will be present in an amount of at least 10% and not more than 80% by weight of the composition.

The composition may include a de-dusting agent, particularly if the composition is in a solid form. Suitable de-dusting agents include dodecyl benzene, tridecyl octadecanoate, trimethylol propane tridodecanoate, twitchel oil, Ensitol USN and mineral oil.

The amount of the composition which is present in the biocide composition may be just sufficient to have an antimicrobial effect or the composition may be present in a substantially greater proportion. It will be appreciated that the biocide composition may be provided as a concentrated solution, emulsion or dispersion which is subsequently diluted for use as an anitmicrobial material. Thus, the amount of the composition of component (a) and the further component which is present in the biocide composition is typically in the range from 0.0001% up to 10% by weight of the biocide composition.

The composition of the present invention is especially effective in providing anti-bacterial activity. Thus, the compositions can be used for the treatment of various media to inhibit the growth of micro-organisms.

As a further aspect of the present invention there is provided a method for inhibiting the growth of micro-organisms on, or in, a medium which comprises treating the medium with a composition of component (a) and the further component as hereinbefore defined.

The composition can be used in conditions in which micro-organisms, especially bacteria, grow and cause problems. Systems in which micro-organisms cause problems include liquid, particularly aqueous, systems such as cooling water liquors, metal working fluids, geological drilling lubricants, polymer emulsions and surface coating compositions such as paints, varnishes and lacquers and also solid materials such as wood and leather. The composition of the present invention can be included in such materials to provide anti-microbial properties. Compositions which include component (c) can be incorporated into a paint, varnish or lacquer to which they can provide anti-fungal characteristics.

As a particular aspect of the present invention there is provided a surface coating composition which contains an effective amount of a composition in accordance with the present invention wherein the composition includes component (c).

The surface coating composition may be a paint, varnish or lacquer and is especially a paint, for example an emulsion paint. The amount of the composition which is present in the surface coating composition is typically in the range from 0.001 up to 2% by weight and especially 0.1 up to 1% by weight relative to the total weight of the surface coating composition. The composition which includes component (c) provides anti-fungal properties to the surface coating composition.

Component (a) and the further component of the composition of the present invention may be the only antimicrobial compounds or may be used together with further compounds having antimicrobial characteristics. The composition may contain more than one compound which is component (a) and/or may contain more than one material which is the further component. Alternatively, a composition of component (a) and the further component in accordance with the present invention may be used together with one or more known antimicrobial compounds. The use of a mixture of antimicrobial compounds can provide a composition having a broader anti-microbial spectrum and hence one which is more generally effective than the components thereof. The known antimicrobial may be one possessing anti-bacterial, anti-fungal, anti-algal or other antimicrobial characteristic. The mixture of the composition of the present invention with other antimicrobial compounds typically contains from 1 to 99% by weight, relative to the weight of total antimicrobially active compounds, of the composition of component (a) and the further component, and particularly from 40 to 60% by weight of the composition of component (a) and the further component.

In our copending, unpublished British Patent Application No. 8811948.2, now published as European Patent Application No. 345955, we disclose a composition which comprises a halogenated aromatic dinitrile, a substituted urea (as in component (b) of the composition of the present invention), and a halogen-containing aromatic alkyl sulphoxide or sulphone (as in component (c) of the composition of the present invention).

Preferred compositions in accordance with our said published European Patent Application have useful anti-fungal and anti-algal activity. We have now found that the activity of these compositions can be increased if used together with the isothiazolinone derivative or isothiazolothione derivative which is component (a) of the composition of the present invention.

Thus, a further aspect of the present invention provides a composition of component (a), component (b) and component (c) together with (d) at least one halogenated aromatic dinitrile.

Component (d) can be a phthalonitrile, an isophthalonitrile or a terephthalonitrile. Suitable material for use as component (d) have the general formula:

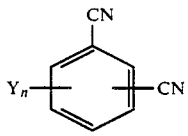

wherein
each Y, which may be the same or different, is a halogen atom; and
n has a value of from one up to four.

When the value of n is less than four, the remaining atoms in the aromatic ring are hydrogen atoms. We have obtained useful results when the value of n is four. Each group Y is preferably a chlorine or fluorine atom. Conveniently all of the groups Y are the same. Compounds which can be used as component (d) of the composition of the present invention are disclosed in U.S. Pat. Nos. 3,290,353 and 3,331,735. As is described in more detail in U.S. Pat. No. 3,290,353, compounds which can be used as component (d) can be prepared by the reaction of the corresponding acid halide, particularly the acid chloride, with ammonia to give the corresponding amide which is then reacted with a dehydrating agent such as phosphorous pentoxide. The foregoing procedure is suitable for the preparation of the chlorinated aromatic dinitrile from which the fluorinated analogue can be prepared by a halogen interchange reaction.

Compounds which can be used as component (d) of the composition of the present invention include tetrachloroisophthalonitrile; tetrafluoroisophthalonitrile and tetrachloroterephthalonitrile. Compositions having useful properties have been obtained in which component (d) is tetrachloroisophthalonitrile.

As examples of other antimicrobial compounds which may be used, together with the compositions in accordance with various aspects of the present invention, there may be mentioned quaternary ammonium compounds such as diethyldodecylbenzyl ammonium chloride; dimethyloctadecyl(dimethylbenzyl)ammonium chloride; dimethyldidecylammonium chloride; dimethyldidodecylammonium chloride; trimethyl-tetradecylammonium chloride; benzyldimethyl($C_{12}$–$C_{18}$ alkyl)ammonium chloride; dichlorobenzyldimethyldodecylammonium chloride; hexadecylpyridinium chloride; hexadecylpyridinium bromide; hexadecyltrimethylammonium bromide; dodecylpyridinium chloride; dodecylpyridinium bisulphate; benzyldodecyl-bis-(beta-hydroxyethyl)ammonium chloride; dodecylbenzyltrimethylammonium chloride; benzyldimethyl($C_{12}$–$C_{18}$ alkyl) ammonium chloride; dodecyldimethylethyl ammonium ethylsulphate; dodecyldimethyl-(1-naphthylmethyl)ammonium chloride; hexadecyldimethylbenzyl ammonium chloride; dodecyldimethylbenzyl ammonium chloride and 1-(3-chloroallyl)-3,5,7-triaza-1-azonia-adamantane chloride; hydantoin derivatives such as 1,3-bis(hydroxymethyl)-5,5-dimethylhydantoin and 1-(hydroxymethyl)-5,5-dimethylhydantoin; amino compounds such as 1,3-bis(2-ethyl hexyl)-5-methyl-5-aminohexahydropyrimidine; hexamethylene tetra amine; 1,3-bis(4-aminophenoxy)propane; and 2-[(hydroxymethyl)-amino]ethanol; imidazole derivatives such as 1[2-(2,4-dichlorophenyl)-2-(2-propenyloxy)ethyl]-1H-imidazole; 2-(methoxycarbonylamino)-benzimidazole; thiocyanate derivatives such as methylene bis thiocyanate; tin compounds or complexes such as tributyltin-oxide, chloride, naphthoate, benzoate or 2-hydroxybenzoate; thiazole derivatives such as 2-(thiocyanomethylthio)-benzthiazole; and mercaptobenzthiazole; nitro compounds such as tris(hydroxymethyl)-nitromethane; 5-bromo-5-nitro-1,3-dioxane and 2-bromo-2-nitropropane-1,3-diol; aldehydes and derivatives such as gluteraldehyde (pentanedial); p-chlorophenyl-3-iodopropargyl formaldehyde and glyoxal; amides such as chloracetamide; N,N-bis(hydroxymethyl)-chloracetamide; N-hydroxymethyl-chloracetamide and dithio-2,2-bis(benzmethyl amide); guanidine derivatives such as poly hexamethylene biguanide and 1,6-hexamethylene-bis[5-(4-chlorophenyl)biguanide]; tjhiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and the salts thereof and 4-hydroxybenzonic acid and the salts and esters thereof and phenol and derivatives thereof such as 5-chloro-2-(2,4-dichlorophenoxy)phenol; thio-bis(4-chlorophenol) and 2-phenylphenol.

Various aspects of the present invention are described in the following illustrative examples.

In the following examples, compositions in accordance with the present invention were subjected to evaluation of the antimicrobial properties of the compositions. The evaluation was effected, under sterile conditions throughout, as follows:

In the microbiological evaluation, various compositions were tested for anti-microbial activity against bacteria using *Pseudomonas aeruginosa*.

MICROBIOLOGICAL EVALUATION

The materials, or mixture of materials, to be tested were added to a nutrient broth in amounts to give a desired concentration of the added material. The added materials were added at concentrations from zero to above the minimum inhibitory concentration of the particular material. In the mixtures, the concentrations of each material were varied in a systematic fashion to give a matrix of mixtures of different relative proportions and different total concentrations.

The effect on the inhibition of growth of bacteria was investigated by inoculating each sample of broth with sufficient of the test bacterium to give about $10^5$ cells $cm^{-3}$. The mixture was incubated at 30° C. for 24 hours. At the end of the test period the presence of turbidity in the broth indicated that growth of the test bacterium had occurred. A lack of turbidity was indicative that no growth had occurred. The lowest concentration of material, or mixture, which stopped all growth was recorded. The results were used to draw an isobologram from which the sum of the fractional inhibitory concentration for a mixture can be determined.

EXAMPLE 1

The microbiological evaluation as described was carried out using the bacterium, *Pseudomonas aeruginosa*. The composition tested was a mixture of 1,2-benzisothiazolin-3-one and 2,3,5,6-tetrachloro-4-(methylsulphonyl)-pyridine.

The concentrations of 1,2-benzisothiazolin-3-one used were 0, 5, 11, 16, 22, 28, 33, 39, 44 and 50 microgram $cm^{-3}$. 2,3,5,6-tetrachloro-4-(methylsulphonyl)- pyridine was used at concentrations of 0, 14, 28, 42, 55, 69, 83, 97, 111 and 125 microgram cm$^{-3}$.

From the results obtained, the lowest sum of FIC was 0.72 which was achieved with a mixture containing 11 microgram cm$^{-3}$ of 1,2-benzisothiazolin-3-one and 28 microgram cm$^{-3}$ of 2,3,5,6-tetrachloro-4-(methylsulphonyl)-pyridine. Details of the mixtures used and the results obtained are set out in Table One.

TABLE ONE

| Mixtures | | |
|---|---|---|
| BIT (a) (ppm) | TCSP (b) (ppm) | FIC |
| 11 | 28 | 0.72 |
| 11 | 42 | 0.84 |
| 11 | 55 | 0.94 |
| 16 | 14 | 0.84 |

Notes to Table One
(a) BIT is 1,2-benzisothiazolin-3-one.
(b) TCSP is 2,3,5,6-tetrachloro-4-(methylsulphonyl)-pyridine.

EXAMPLE 2

The procedure of Example 1 was repeated with the exception that the 2,3,5,6-tetrachloro-4-(methylsulphonyl)pyridine was replaced by di-iodomethyl-4-methylphenyl sulphone.

The concentrations of 1,2-benzisothiazolin-3-one used were 0, 5, 11, 16, 22, 28, 33, 39, 44 and 50 microgram cm$^{-3}$. Di-iodomethyl-4-methylphenyl sulphone was used at concentrations of 0, 55, 111, 166, 221, 277, 332, 388, 444 and 500 microgram cm$^{-3}$.

From the results obtained, the lowest sum of FIC was 0.56 which was achieved with a mixture containing 11 microgram cm$^{-3}$ of 1,2-benzisothiazolin-3-one and 111 microgram cm$^{-3}$ of di-iodomethyl-4-methylphenyl sulphone. Details of the mixtures used and the results obtained are set out in Table Two.

TABLE TWO

| Mixtures | | |
|---|---|---|
| BIT (a) (ppm) | DIMS (c) (ppm) | FIC |
| 5 | 277 | 0.71 |
| 11 | 111 | 0.56 |
| 11 | 166 | 0.83 |
| 11 | 221 | 0.94 |
| 16 | 55 | 0.6 |

Notes to Table Two
(a) is as defined in Notes to Table One.
(c) DIMS is di-iodomethyl-4-methylphenyl sulphone.

EXAMPLE 3

The procedure of Example 1 was repeated with the exception that 2,3,5,6-tetrachloro-4-(methylsulphonyl)-pyridine was replaced by 3-(3,4-dichlorophenyl)-1,1-dimethylurea.

The concentrations of 1,2-benzisothiazolin-3-one used were 0, 5, 11, 16, 22, 28, 33, 39, 44 and 50 microgram cm$^{-3}$. 3-(3,4-dichlorophenyl)-1,1-dimethylurea was used at concentrations of 0, 55, 111, 166, 221, 277, 332, 388, 444 and 500 microgram cm$^{-3}$.

From the results obtained, the lowest sum of FIC was 0.56 which was achieved with a mixture containing 5 microgram cm$^{-3}$ of 1,2-benzisothiazolin-3-one and 166 microgram cm$^{-3}$ of 3-(3,4-dichlorophenyl)-1,1-dimethylurea. Details of the mixtures used and the results obtained are set out in Table Three.

TABLE THREE

| Mixtures | | |
|---|---|---|
| BIT (a) (ppm) | DCDMU (d) (ppm) | FIC |
| 5 | 166 | 0.56 |
| 11 | 111 | 0.72 |
| 16 | 55 | 0.84 |

Notes to Table Three
(a) is as defined in Notes to Table One.
(d) DCDMU is 3-(3,4-dichlorophenyl)-1,1-dimethylurea.

EXAMPLE 4

The procedure of Example 1 was repeated with the exception that 2,3,5,6-tetrachloro-4-(methylsulphonyl)-pyridine was replaced by a mixed biocide composition having a composition of 40% by weight of tetrachloroisophthalonitrile, 40% by weight of 2,3,5,6-tetrachloro-4-(methylsulphonyl)-pyridine and 20% by weight of 3-(3,4-dichlorophenyl)-1,1-dimethylurea.

The biocide composition was prepared by mixing the components together by grinding in a mortar and pestle.

The concentrations of 1,2-benzisothiazolin-3-one used were 0, 5, 11, 16, 22, 28, 33, 39, 44 and 50 microgram cm$^{-3}$. The mixed biocide was used at concentrations of 0, 55, 111, 167, 222, 278, 333, 389, 444 and 500 microgram cm$^{-3}$, the weights being weight of the total mixed biocide composition.

From the results obtained, the lowest sum of FIC was 0.63 which was achieved with a mixture containing 16 microgram cm$^{-3}$ of 1,2-benzisothiazolin-3-one and 55 microgram cm$^{-3}$ of the mixed biocide composition. Details of the mixtures used and the results obtained are set out in Table Four.

TABLE FOUR

| Mixtures | | |
|---|---|---|
| BIT (a) (ppm) | MBC-1 (e) (ppm) | FIC |
| 16 | 55 | 0.63 |
| 16 | 111 | 0.77 |
| 16 | 167 | 0.91 |
| 22 | 55 | 0.81 |

Notes to Table Four
(a) is as defined in Notes to Table One.
(e) MBC-1 is the mixed biocide composition described in Example 4.

EXAMPLE 5

The procedure of Example 4 was repeated using a mixed biocide composition prepared in the same manner but having a different composition, namely 30% by weight of tetrachloro-isophthalonitrile, 30% by weight of 2,3,5,6-tetrachloro-4-(methyl-sulphonylphenyl)-pyridine, 20% by weight of 3-(3,4-dichlorophenyl)-1,1-dimethylurea and 20% by weight of zinc oxide.

The concentrations of 1,2-benzisothiazolin-3-one used were 0, 5, 11, 16, 22, 28, 33, 39, 44 and 50 microgram cm$^{-3}$. The mixed biocide was used at concentrations of 0, 28, 55, 83, 111, 139, 166, 194, 222 and 250 microgram cm$^{-3}$, the weights being weight of the total mixed biocide composition, including zinc oxide.

From the results obtained, the lowest sum of FIC was 0.57 which was achieved with a mixture containing 11 microgram cm$^{-3}$ of 1,2-benzisothiazolin-3-one and 111 microgram cm$^{-3}$ of the mixed biocide composition. Details of the mixtures used and the results obtained are set out in Table Five.

TABLE FIVE

| Mixtures | | |
|---|---|---|
| BIT (a) (ppm) | MBC-2 (f) (ppm) | FIC |
| 11 | 111 | 0.57 |
| 16 | 28 | 0.89 |

Notes to Table Five
(a) is as defined in Notes to Table One.
(f) MBC-2 is the mixed biocide composition described in Example 5.

EXAMPLE 6

The procedure of Example 4 was repeated using a mixed biocide composition prepared in the same manner but having a different composition namely 55% by weight of tetrachloro-isophthalonitrile, 20% by weight of di-iodomethyl-4-methylphenyl sulphone and 25% by weight of 3-(3,4-dichlorophenyl)-1,1-dimethyl urea.

The concentrations of 1,2-benzisothiazolin-3-one used were 0, 5, 11, 16, 22, 28, 33, 39, 44 and 50 microgram $cm^{-3}$. The mixed biocide was used at concentrations of 0, 28, 55, 83, 111, 139, 166, 194, 222 and 250 microgram $cm^{-3}$, the weights being weight of the total mixed biocide composition.

From the results obtained, the lowest sum of FIC was 0.58 which was achieved with a mixture containing 11 microgram $cm^{-3}$ of 1,2-benzisothiazolin-3-one and 55 microgram $cm^{-3}$ of the mixed biocide composition. Details of the mixtures used and the results obtained are set out in Table Six.

TABLE SIX

| Mixtures | | |
|---|---|---|
| BIT (a) (ppm) | MBC-3 (g) (ppm) | FIC |
| 5 | 166 | 0.90 |
| 11 | 55 | 0.58 |
| 11 | 83 | 0.71 |
| 11 | 139 | 0.96 |
| 16 | 28 | 0.61 |
| 22 | 28 | 0.79 |

Notes to Table Six
(a) is as defined in Notes to Table One.
(g) MBC-3 is the mixed biocide composition described in Example 6.

EXAMPLE 7

The procedure of Example 4 was repeated using a mixed biocide composition prepared in the same manner but having a different composition namely 35% by weight of tetrachloro-isophthalonitrile, 20% by weight of di-iodomethyl-4-methylphenyl sulphone, 25% by weight of 3-(3,4-dichlorophenyl)-1,1-dimethylurea and 20% by weight of zinc oxide.

The concentrations of 1,2-benzisothiazolin-3-one used were 0, 5, 11, 16, 22, 28, 33, 39, 44 and 50 microgram $cm^{-3}$. The mixed biocide was used at concentrations of 0, 28, 55, 83, 111, 139, 166, 194, 222 and 250 microgram $cm^{-3}$, the weights being weight of the total mixed biocide composition including zinc oxide.

From the results obtained, the lowest sum of FIC was 0.77 which was achieved with a mixture containing 16 microgram $cm^{-3}$ of 1,2-benzisothiazolin-3-one and 28 microgram $cm^{-3}$ of the mixed biocide composition. Details of the mixtures used and the results obtained are set out in Table Seven.

TABLE SEVEN

| Mixtures | | |
|---|---|---|
| BIT (a) (ppm) | MBC-4 (h) (ppm) | FIC |
| 5 | 111 | 0.98 |
| 11 | 83 | 0.99 |
| 16 | 55 | 0.97 |
| 16 | 28 | 0.77 |

Notes to Table Seven
(a) is as defined in Notes to Table One.
(h) MBC-4 is the mixed biocide composition described in Example 7.

EXAMPLE 8

The procedure of Example 5 was repeated with the exception that 1,2-benzisothiazolin-3-one was replaced by 2-methyl-4,5-trimethylene-4-isothiazolin-3-one.

The concentrations of 2-methyl-4,5-trimethylene-4-isothiazolin-3-one used were 0, 5, 11, 16, 22, 28, 33, 39, 44 and 50 microgram $cm^{-3}$. The mixed biocide was used at concentrations of 0, 14, 28, 55, 83, 111, 139, 166, 194, 222 and 250 microgram $cm^{-3}$, the weights being weight of the total mixed biocide composition, including zinc oxide.

From the results obtained, the lowest sum of FIC was 0.51 which was achieved with a mixture containing 5 microgram $cm^{-3}$ of 2-methyl-4,5-trimethylene-4-isothiazolin-3-one and 55 microgram $cm^{-3}$ of the mixed biocide composition. Details of the mixtures used and the results obtained are set out in Table Eight.

TABLE EIGHT

| Mixtures | | |
|---|---|---|
| MTI (i) (ppm) | MBC-2 (f) (ppm) | FIC |
| 5 | 55 | 0.51 |
| 11 | 28 | 0.56 |
| 16 | 14 | 0.65 |

Notes to Table Eight
(f) is as defined in Notes to Table Five.
(i) MTI is 2-methyl-4,5-trimethylene-4-isothiazolin-3-one.

EXAMPLES 9 to 11

An aqueous dispersion was prepared by wet milling together 9% by weight of tetrachloroisophthalonitrile; 6% by weight of 3-(3,4-dichlorophenyl)-1,1-dimethylurea; 9% by weight of 2,3,5,6-tetrachloro-4-(methylsulphonyl)-pyridine; 6% by weight of zinc oxide; 10% by weight of propylene glycol; 3% by weight of an ethylene oxide-propylene oxide-ethylene oxide block copolymer containing 44% by weight of ethylene oxide units and wherein the average molecular weight of the propylene oxide block is 2700; and water to 100% by weight.

The above aqueous dispersion was mixed with an aqueous dispersion, at pH 6 to 8, containing 33% w/v of 1,2-benzisothiazolin-3-one, by stirring together the two dispersions. The dispersions were mixed in different proportions, as set out in Table Nine.

TABLE NINE

| | Mixture (parts by volume) (j) | |
|---|---|---|
| Example | BD | ND |
| 9 | 1 | 10 |
| 10 | 1 | 15 |

TABLE NINE-continued

| Example | Mixture (parts by volume) (j) | |
|---------|------|------|
|         | BD   | ND   |
| 11      | 1    | 20   |

Notes to Table Nine
(j) BD is the aqueous dispersion containing 33% w/v of 1,2-benzisothiazolin-3-one. ND is the aqueous dispersion including tetrachloroisophthalo-nitrile, 3-(3,4-dichlorophenyl)-1,1-dimethylurea, 2,3,5,6-tetrachloro-4-(methylsulphonyl)-pyridine and zinc oxide.

The mixing ratios are in respect of the total volume of each aqueous dispersion.

EXAMPLES 12 to 20

The mixed dispersions of Examples 9 to 11 were added to 50 g aliquots of an exterior acrylic emulsion paint (based on Revacryl 1A latex at pH 9) containing 0.2% yeast extract. The mixed dispersions were added to the paint in amounts to give a level of 1,2-benzisothiazolin-3-one of 100, 200 or 300 ppm w/v in the paint. The paint mixture containing the added mixed dispersions was then inoculated with a mixture of bacteria.

The inoculum was a mixed suspension of bacteria which had been prepared by mixing equal amounts of suspensions each of which contained a different one of the bacteria *Aeromonas hydrophila, Proteus rettgeri, Pseudomonas aeruginosa, Serratia marcescens, Alcaligenes spp, Pseudomonas cepacia* and *Pseudomonas putida*.

Each paint mixture was inoculated with 1 cm$^3$ of the mixed bacterial suspension and incubated at 30° C. After contact times of one, three and seven days, a small aliquot of the paint mixture was removed and examined for bacterial growth. The extent of growth of bacteria was recorded. After removal of the seven day aliquot, a further 1 cm$^3$ of the mixed bacterial suspension was added. Aliquots were removed after one, three and seven days of the second week. At the end of the second week, a further 1 cm$^3$ of the mixed bacterial suspension was added. Aliquots were removed after one, three and seven days of the third week. The results obtained are set out hereafter in Table Ten.

For comparative purposes, further paint mixtures were prepared which contained only the dispersion of 1,2-benzisothiazolin-3-one or only the dispersion including
tetrachloroisophthalonitrile;
3-(3,4-dichlorophenyl)-1,1-dimethylurea;
2,3,5,6-tetrachloro-4-(methylsulphonyl)-pyridine and zinc oxide.

The results of tests using these comparative paint mixtures are also set out in Table Ten.

TABLE TEN

| Ex. or Comp Ex | Disp (j) (k) Type | (ppm) (l) | Bacterial growth (m) | | | | | | | | |
|---|---|---|---|---|---|---|---|---|---|---|---|
|   |   |   | Week 1 Day | | | Week 2 Day | | | Week 3 Day | | |
|   |   |   | 1 | 3 | 7 | 1 | 3 | 7 | 1 | 3 | 7 |
| 12 | 9 | 300 | 0 | 0 | 0 | 0 | 0 | 0 | 2 | 0 | 0 |
| 13 | 9 | 200 | 0 | 0 | 0 | 4 | 0 | 0 | 4 | 2 | 0 |
| 14 | 9 | 100 | 3 | 1 | 0 | 4 | 3 | 1 | 4 | 4 | 4 |
| 15 | 10 | 300 | 0 | 0 | 0 | 0 | 0 | 0 | 1 | 0 | 0 |
| 16 | 10 | 200 | 0 | 0 | 0 | 2 | 0 | 0 | 3 | 0 | 0 |
| 17 | 10 | 100 | 1 | 0 | 0 | 4 | 0 | 0 | 4 | 3 | 0 |
| 18 | 11 | 300 | 0 | 0 | 0 | 0 | 0 | 0 | 0 | 0 | 0 |
| 19 | 11 | 200 | 0 | 0 | 0 | 1 | 0 | 0 | 2 | 0 | 0 |
| 20 | 11 | 100 | 1 | 0 | 0 | 4 | 0 | 0 | 4 | 0 | 0 |
| A | BD | 300 | 0 | 0 | 0 | 3 | 3 | 3 | 3 | 3 | 0 |
| B | BD | 200 | 2 | 1 | 0 | 4 | 3 | 1 | 4 | 4 | 3 |
| C | BD | 100 | 4 | 4 | 4 | 4 | 4 | 4 | NM | NM | NM |
| D | ND | 2* | 0 | 0 | 0 | 4 | 2 | 2 | 4 | 4 | 4 |
| E | ND | 1* | 4 | 4 | 2 | 4 | 4 | 4 | NM | NM | NM |
| F | ND | 0.5* | 4 | 4 | 4 | 4 | 4 | 4 | NM | NM | NM |
| G | ND | 0.25* | 4 | 4 | 4 | 4 | 4 | 4 | NM | NM | NM |
| H | NIL | NIL | 4 | 4 | 4 | 4 | 4 | 4 | 4 | 4 | 4 |

Notes to Table Ten
(j) is as defined in Notes to Table Nine
(k) 9, 10 and 11 are the dispersions of Examples 9, 10 and 11.
(l) The quantities are given as ppm w/v relative to the paint mixture of the 1,2-benzisothiazolin-3-one component of the aqueous dispersion.
*These quantities are given as a % w/v relative to the paint mixture of the total aqueous dispersion identified as ND.
(m) 0 means no growth (no visible colonies). 1 means a trace of growth visible. 2 means a light growth (a few colonies visible). 3 means moderate growth (discrete colonies visible, possibly with some coalescence). 4 means dense/confluent growth (coalescing colonies visible throughout). NM means no measurement made since previous results indicated no residual activity.

EXAMPLES 21 to 29

The procedure described for Examples 12 to 20 was repeated with the exception that the acrylic emulsion paint containing yeast extract was replaced by a polyvinylacetate aqueous emulsion paint formulation which did not contain yeast extract.

The results obtained are set out hereafter in Table Eleven.

TABLE ELEVEN

| Ex. or Comp Ex | Disp (j) (k) Type | (ppm) (l) | Bacterial growth (m) | | | | | | | | |
|---|---|---|---|---|---|---|---|---|---|---|---|
|   |   |   | Week 1 Day | | | Week 2 Day | | | Week 3 Day | | |
|   |   |   | 1 | 3 | 7 | 1 | 3 | 7 | 1 | 3 | 7 |
| 21 | 9 | 300 | 0 | 0 | 0 | 1 | 0 | 0 | 3 | 4 | 4 |
| 22 | 9 | 200 | 0 | 0 | 0 | 3 | 3 | 4 | NM | NM | NM |
| 23 | 9 | 100 | 1 | 0 | 1 | 4 | 4 | 4 | NM | NM | NM |

TABLE ELEVEN-continued

| Ex. or Comp Ex | Disp (j) Type | (k) (ppm) (l) | Week 1 Day 1 | 3 | 7 | Week 2 Day 1 | 3 | 7 | Week 3 Day 1 | 3 | 7 |
|---|---|---|---|---|---|---|---|---|---|---|---|
| 24 | 10 | 300 | 0 | 0 | 0 | 0 | 0 | 0 | 2 | 3 | 3 |
| 25 | 10 | 200 | 0 | 0 | 0 | 0 | 0 | 0 | 3 | 4 | 4 |
| 26 | 10 | 100 | 0 | 0 | 0 | 2 | 2 | 4 | 4 | 4 | 4 |
| 27 | 11 | 300 | 0 | 0 | 0 | 0 | 0 | 0 | 0 | 0 | 0 |
| 28 | 11 | 200 | 0 | 0 | 0 | 0 | 0 | 0 | 1 | 0 | 0 |
| 29 | 11 | 100 | 0 | 0 | 0 | 4 | 4 | 4 | NM | NM | NM |
| I | BD | 300 | 2 | 2 | 0 | 2 | 1 | 4 | 4 | 4 | 4 |
| J | BD | 200 | 4 | 4 | 4 | 4 | 4 | 4 | NM | NM | NM |
| K | BD | 100 | 4 | 4 | 4 | 4 | 4 | 4 | NM | NM | NM |
| L | ND | 2* | 3 | 4 | 4 | 4 | 4 | 4 | NM | NM | NM |
| M | ND | 1* | 4 | 4 | 4 | 4 | 4 | 4 | NM | NM | NM |
| N | ND | 0.5* | 4 | 4 | 4 | 4 | 4 | 4 | NM | NM | NM |
| O | ND | 0.25* | 4 | 4 | 4 | 4 | 4 | 4 | NM | NM | NM |
| P | NIL | NIL | 4 | 4 | 4 | 4 | 4 | 4 | 4 | 4 | 4 |

Notes to Table Eleven
(j) is as defined in Notes to Table Nine.
(k), (l) and (m) are all as defined in Notes to Table Ten.

We claim:
1. A biocidal composition which comprises
(a) at least one isothiazolinone derivative or at least one isothiazolothione derivative, and at least one compound which is
(b) at least one substituted urea having the formula

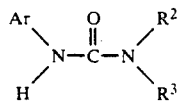

or
(c) at least one halogen-containing aromatic alkyl sulphoxide or sulphone having the formula $$Ar^1SO_xR^4$$

wherein
Ar is an aryl, substituted aryl, heteroaryl, substituted heteroaryl, heterocyclic or substituted heterocyclic group;
$R^2$ is an alkyl, substituted alkyl, alkenyl, substituted alkenyl, alkynyl, substituted alkynyl, cycloalkyl, substituted cycloalkyl, alkoxy or substituted alkoxy group;
$R^3$ is a hydrogen atom or a group as defined for $R^2$;
$Ar^1$ is an aryl, substituted aryl, heteroaryl, substituted heteroaryl, heterocyclic or substituted heterocyclic group;
$R^4$ is an alkyl, substituted alkyl, aryl or substituted aryl group;
x as a value of one or two; and
at least one of the groups $Ar^1$ and $R^4$ contains at least one halogen substituent; and
wherein the composition contains from 1 to 99% by weight of (a) and correspondingly from 99 to 1% by weight of (b) or (c) or mixture of (b) and (c).
2. The biocidal composition of claim 1 in which (a) is at least one compound of the general formula:

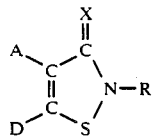

wherein:
X is an oxygen or sulphur atom;
R is a hydrogen atom, a substituted or unsubstituted hydrocarbyl group, a substituted or unsubstituted hydrocarbylthio group, a substituted or unsubstituted hydrocarbyloxy group, a carbamoyl group or a cation;
A is a hydrogen atom, a halogen atom, a cyano group, or a substituted or unsubstituted hydrocarbyl group; or
D is a hydrogen atom, a halogen atom, a cyano group, or a substituted or unsubstituted hydrocarbyl group; or
A and D together with the carbon atoms to which they are attached, form a five- or six-membered ring, which may be substituted.
3. The biocidal composition of claim 2 in which component (a) is a compound in which X is an oxygen atom and; R is a hydrogen atom, an alkyl group containing 1 to 4 carbon atoms, or a monovalent cation which is an alkali metal, an amine or a quaternary ammonium.
4. The biocidal composition of claim 3 in which component (a) is a compound in which A and D together with the carbon atoms to which they are attached, form a substituted or unsubstituted five- or six-membered hydrocarbon ring.
5. The biocidal composition of claim 2 in which component (a) is selected from 2-methylisothiazolin-3-one; 5-chloro-2-methylisothiazolin-3-one; 4,5-dichloro-2-methylisothiazolin-3-one; 1,2-benzisothiazolin-3-one; 4,5-trimethylene-4-isothiazolin-3-one and 2-methyl-4,5-trimethylene-4-isothiazolin-3-one.
6. The biocidal composition of claim 1 in which component (b) is a compound in which the group Ar contains at least one substituent which is a halogen atom, an alkyl group, an alkoxy group or an aryloxy group and the substituent group may be further substituted by a substituent selected from the same group of substituents.

7. The biocidal composition of claim 1 in which component (b) is a compound in which R² and R³ are unsubstituted and each contains not more than six carbon atoms.

8. The composition of claim 1 in which component (b) is 3-(3,4-dichlorophenyl)-1,1-dimethylurea, 3-(3,4-dichlorophenyl)-1-methyl-1-n-butylurea, 3-(3-chloro-4-bromophenyl)-1-methyl-1-methoxyurea, 3-[4-(4'-chlorophenoxy)phenyl]-1,1-dimethylurea, 3-[4-(4'-methoxyphenoxy)phenyl]-1,1-dimethylurea, 3-(4-chlorophenyl)-1-methyl-1-(3-butynyl)urea, 3-phenyl-1-(2-methylcyclohexyl)urea, or 3-(benzothiazol-2-yl)-1-methylurea.

9. The biocidal composition of claim 1 in which component (c) is a compound wherein Ar¹ is a pyridine ring which contains at least one halogen substituent and R⁴ is an unsubstituted alkyl group containing 1 to 12 carbon atoms or Ar¹ contains an aryl group, R⁴ is a halogen substituted methyl group and x has a value of two.

10. The biocidal composition of claim 11 in which component (c) is
2,3,5,6-tetrachloro-4-(methylsulphonyl)pyridine;
2,3,6-trichloro-4-(methylsulphonyl)pyridine;
2,3,5,6-tetrachloro-4-(isopropylsulphonyl)pyridine or
di-iodomethyl-4-methylphenyl sulphone.

11. The biocidal composition of claim 1 which comprises (a) 1,2-benzisothiazolin-3-one; and at least one compound which is (b) 3-(3,4-dichlorophenyl)-1,1-dimethylurea; or (c) di-iodomethyl-4-methylphenyl sulphone.

12. The biocidal composition of claim 1 which includes a further component (d) which is an antimicrobial compound which is at least one halogenated aromatic dinitrile of the formula:

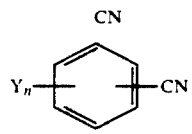

where
each Y, which may be the same or different, is a halogen atom; and
n has a value of from one up to four;
wherein said dinitrile comprises between about 15% and about 53% by weight of the total weight of components (a), (b), (c) and (d).

13. The biocidal composition of claim 15 in which the dinitrile is tetrachloroisophthalonitrile, tetrafluoroisophthalonitrile or tetrachloroterephthalonitrile.

14. The biocidal composition of claim 15 which comprises 1,2-benzisothiazolin-3-one; 3-(3,4-dichlorophenyl)-1,1-dimethylurea; di-iodomethyl-4-methylphenyl sulphone and tetrachloroisophthalonitrile.

15. A medium which is susceptible to attack by micro-organisms and which contains from 0.0001 to 10% by weight of the medium of the biocidal composition of claim 1, which medium is selected from cooling water liquors, metal working fluids, geological drilling lubricants, polymer emulsions, paints, varnishes, lacquers, wood and leather.

16. A method for inhibiting the growth of micro-organisms on, or in, a medium in which micro-organisms grow, which comprises treating the medium with the biocidal composition of claim 1, which medium is selected from cooling water liquors, metal working fluids, geological drilling lubricants, polymer emulsions, paints, varnishes, lacquers, wood and leather.

* * * * *

UNITED STATES PATENT AND TRADEMARK OFFICE
CERTIFICATE OF CORRECTION

PATENT NO. : 5,125,967
DATED : June 30, 1992
INVENTOR(S) : Fraser F. Morpeth & Malcolm Greenhalgh It is certified that error appears in the above-identified patent and that said Letters Patent is hereby corrected as shown below:

Column 20, line 15 (claim 13, first line) "The biocidal composition of claim 15" should read as --The biocidal composition of claim 12--

Column 20, line 18 (claim 14, first line) "The biocidal composition of claim 15" should read as --The biocidal composition of claim 12--

Signed and Sealed this

Twenty-first Day of September, 1993

Attest:

BRUCE LEHMAN

*Attesting Officer*  *Commissioner of Patents and Trademarks*